United States Patent [19]

Hässlin

[11] Patent Number: 5,674,514
[45] Date of Patent: Oct. 7, 1997

[54] STORAGE STABLE PESTICIDAL AQUEOUS EMULSIONS

[75] Inventor: Hans Walter Hässlin, Grenzach-Whylen, Germany

[73] Assignee: Ciba-Geigy Corporation, Tarrytown, N.Y.

[21] Appl. No.: 105,192

[22] Filed: Aug. 9, 1993

Related U.S. Application Data

[63] Continuation-in-part of Ser. No. 948,523, Sep. 21, 1992, abandoned.
[51] Int. Cl.$^6$ ............................................. A01N 25/04
[52] U.S. Cl. ...................... 424/405; 514/937; 514/772.1; 514/75; 514/68
[58] Field of Search ..................... 424/405; 514/937, 514/772.1–776.1, 788.1, 789, 75, 68

[56] References Cited

U.S. PATENT DOCUMENTS

| | | | |
|---|---|---|---|
| 4,818,536 | 4/1989 | Meyers et al. | 424/409 |
| 4,828,835 | 5/1989 | Meyers et al. | 424/409 |
| 4,938,797 | 7/1990 | Hasslin et al. | 71/118 |
| 5,139,152 | 8/1992 | Hodakowski et al. | 206/524.7 |

FOREIGN PATENT DOCUMENTS

| | | |
|---|---|---|
| 0224846 | 6/1987 | European Pat. Off. . |
| 369613 | 5/1990 | European Pat. Off. . |
| 2115285 | 9/1983 | United Kingdom . |
| 8903175 | 4/1989 | WIPO . |

OTHER PUBLICATIONS

Chem. Abst. 107:149231m, Albrecht et al., 1987.

*Primary Examiner*—Neil S. Levy
*Attorney, Agent, or Firm*—Marla J. Mathias; William A. Teoli, Jr.

[57] ABSTRACT

Aqueous emulsions are described comprising an organic phase of a substantially hydrophobic pesticide or mixture of pesticides which are liquid or dissolved in a hydrophobic solvent, and an aqueous phase comprising surfactants and/or dispersants, wherein a) the emulsion is in the form of an aqueous concentrate, and
b) an emulsion-stabilizing amount of a polymer or polymer mixture is present which is more soluble in the organic phase than in the aqueous phase.

28 Claims, No Drawings

5,674,514

STORAGE STABLE PESTICIDAL AQUEOUS EMULSIONS

This is a continuation-in-part of Ser. No. 948,523, filed Sep. 21, 1992, now abandoned.

The present invention relates to pesticidal aqueous emulsions, the preparation of said emulsions and a method of using said emulsions to combat pests or as plant growth regulators.

Non-aqueous, but water-emulsifiable agricultural chemical concentrates which can be liquid or solid are described, for example, in U.S. Pat. Nos. 4,818,536 and 4,828,835 with and without a water-immiscible organic solvent respectively, and including a polymer. The polymer functions as a reservoir for the controlled release of the agricultural chemical after dispersing by spraying. The emulsion concentrates can be diluted to form aqueous emulsions but the storage stability of the resulting aqueous emulsions is only a matter of hours.

Insecticidal compositions suitable for use as concentrates for the preparation of sprays are described, for example, in EP 369 613. Said compositions are non-aqueous and comprise an active substance, a polymeric substance and a carrier solvent, the latter being present in a substantial amount.

Aqueous pesticide concentrates have only a limited storage stability. It is therefore most desirable for practical purposes to provide highly storage-stable aqueous pesticide concentrates having no organic solvents or only solvent amounts to dissolve a crystalline pesticide and which can be diluted easily with pure water, thereby forming stable dilute emulsions for application purposes. An aqueous emulsion concentrate which is stable under storage for at least two years is desired.

The object of the present invention was therefore to provide a highly storage-stable aqueous emulsion concentrate, provide an environmentally more acceptable formulation, and reduce the risk of inflammation or toxicity to mammals.

It has now been found that aqueous emulsions containing a high concentration of pesticide can be prepared which provide much improved storage stability. The stability of the emulsion is achieved by dissolving a polymeric substance in the pesticide and converting the mixture to a fine-particle emulsion using a high shear mixer. Surprisingly there is neither growth in the particle size over time nor phase separation of the emulsion components. Furthermore a greater ease of use is possible because the emulsion itself is diluted after which particle size remains substantially unchanged.

One object of the invention is to provide an aqueous emulsion comprising an organic phase of a substantially hydrophobic pesticide or mixture of pesticides which are liquid or dissolved in a hydrophobic solvent, and an aqueous phase comprising surfactants and/or dispersants, characterized in that a) the emulsion is in the form of an aqueous concentrate, and
b) an emulsion-stabilising amount of a polymer or polymer mixture is present which is more soluble in the organic phase than in the aqueous phase.

The pesticide or a mixture of pesticides is/are liquid at ambient temperature or can be liquefied by warming, and substantially insoluble in water. If the polymer does not dissolve in the pesticide there may be additionally used a hydrophobic solvent for example an aliphatic or aromatic hydrocarbon or halogenated hydrocarbon; some examples are xylene, cyclohexane, cyclohexanone and glycerintriacetate.

The term pesticide is understood to encompass herbicides, insecticides, acaricides, nematicides, ectoparasiticides and fungicides. Examples of compound classes to which the pesticide in the emulsion may belong include ureas, triazines, triazoles, carbamates, phosphoric acid esters, dinitroanilines, morpholines, acylalanines, pyrethroids, benzilic acid esters, diphenylethers and polycyclic halogenated hydrocarbons.

Specific examples of pesticides (using the common name) suitable for the emulsions according to the invention are listed below (Pesticide Manual, 9th Edition, British Crop Protection Council):

Ureas

Triasulfuron, Chlorobromuron, Chloroxuron, Chlorotoluron, Fluometuron, Thiazafluron.

Haloacetanilides

Metolachlor (2-chloro-6'-ethyl-N-(2-methoxy-1-methylethyl)acet-o-toluidide), Pretilachlor, Dimethachlor, Alachlor, Propachlor, Trimexachlor.

s-Triazines

Atrazin, Propazin, Terbutylazin, Ametryn, Aziprotryn, Cyromazin.

Triazole Derivatives

Propiconazol ((±)-1[2-(2,4-dichlorophenyl)-4-propyl-1,3-dioxolan-2-ylmethyl]-1H-1,2,4-triazole), Etaconazol, 1-[2-(2,4-dichlorophenyl)-pent-1-yl]-1H-1,2,4-triazole, Triadimefon, Difenoconazol, Penconazol (1-(2,4-dichloro-β-propylphenethyl)-1H-1,2,4-triazole)

Carbamates

Dioxacarb, Ethiofencarb, Furathiocarb, Aldicarb, Benomyl, 2-sec-butylphenylmethylcarbamate.

Phosphoric Acid Ester

Diazinon (O,O-diethyl O-2-isopropyl-6-methylpyrimidin-4-yl phosphorothioate), Methidathion, Isazofos (O-5-chloro-1-isopropyl-1H-1,2,4-triazol-3-yl O,O-diethyl phosphorothioate), Piperophos, Anilofos, Azinphos methyl, Isofenphos, Parathion, Malathion, Demeton, Fenamiphos, Fenthion, Fenitrothion, Fenchlorphos, Chlorfenvinphos (2-chloro-1-(2,4-dichloro-phenyl)vinyl diethyl phosphate), Profenofos (O-4-bromo-2-chlorophenyl O-ethyl S-propyl phosphorothioate), Azamethiphos, Methacrifos.

Dinitroanilines

Pendimethalin, Isopropalin, Butralin, Fluchloralin, Profluralin.

Acylalanines

Metalaxyl, Fluralaxyl, Benzoylprop ethyl, Flamprop methyl.

Pyrethroids

Permethrin, Cypermethrin ((RS)-α-cyano-3-phenoxybenzyl(1RS)-cis-trans-3-(2,2-dichlorovinyl)-1,1-dimethyl-cyclopropanecarboxylate), Fluvalinate, Resmethrin, Fenvalerate, Fluvalinate, Tetramethrin, Cyhalotrin.

Benzilic Acid Esters

Bromopropylate, Chlorbenzylate, Chlorpropylate.

Diphenylether

Cis,trans-(±)-2-ethyl-5-(4-phenoxy-phenoxymethyl)-1,3-dioxolane.

Oxime

Pyrifenox (2',4'-dichloro-2-(3-pyridyl)acetophenone O-methyloxime)

Miscellaneous

Methopren, Flupropimorph, Tridemorph, Bromoxynil, Oxadiazon, Bupyrimate, Dicofol, Fenpropidin ((RS)-1-[3-(4-tert-butylphenyl)-2-methylpropyl]piperidine), Fenpropimorph, Fenoxycarb.

Preferred pesticides are O,O-diethyl O-2-isopropyl-6-methylpyrimidin-4-yl phosphorothioate, 2-chloro-6'-ethyl-N-(2-methoxy-1-methylethyl)acet-o-toluidide, O-5-chloro-1-isopropyl-1H-1,2,4-triazol-3-yl O,O-diethyl phosphorothioate, 2',4'-dichloro-2-(3-pyridyl)acetophenone O-methyloxime and cis,trans-(±)-2ethyl-5-(4-phenoxy-phenoxymethyl)-1,3-dioxolane.

Suitable polymers in the practise of the invention are those which are substantially insoluble in water, essentially stable to hydrolysis, and dissolve in the pesticide or pesticide mixture or in a solution of at least one pesticide in a hydrophobic solvent, thereby increasing its viscosity. The polymer molecular weight, as measured by viscosity or light scattering, lies between 10,000 and 1,000,000 daltons, preferably 30,000 to 300,000 daltons.

Suitable polymers may be selected from the following polymers, copolymers or mixtures thereof:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), for example high density polyethylene (HDPE), low density polyethylene (LDPE) and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers linear low density polyethylene (LLDPE) and mixtures thereof with low density polyethylene (LDPE), propylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned in 1) above, for example polypropylene/ethylene propylene copolymers, LDPE/EVA, LDPE/EAA, LLDPE/EVA and LLDPE/EAA.

3a. Hydrocarbon resins (for example $C_5$–$C_9$), including hydrogenated modifications thereof.

4. Polystyrene, poly-(p-methylstyrene), poly-(α-methylstyrene).

5. Copolymers of styrene or α-methylstyrene with dienes or acrylic derivatives, for example styrene/butadiene, styrene/acrylonitrile, styrene/alkylmethacrylate, styrene/butadiene/alkylacrylate, styrene/maleic anhydride, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or α-methylstyrene, for example styrene on polybutadiene, styrene on polybutadiene/styrene or polybutadiene/acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyalkylacrylates or polyalkylmethacrylates, styrene and acrylonitrile on acrylate/butadiene copolymers, as well as mixtures thereof with the copolymers listed under 5), for example the copolymer mixtures known as ABS, MBS, ASA or AES polymers.

7. Halogenated polymers such as polychloroprene, chlorinated rubbers, chlorinated or sulfochlorinated polyethylene, copolymers of ethylene and chlorinated ethylene, epichlorohydrin homo- and copolymers, preferably polymers of halogenated vinyl compounds, for example polyvinylchloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from α,β-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkylacrylate copolymers, acrylonitrile/alkoxyalkylacrylate or acrylonitrile/vinyl halide copolymers or acrylonitrile/alkylmethacrylate/butadiene terpolymers.

10. Polymers derived from unsaturated alcohols and amines or the acyl derivatives or acetals thereof, such as polyvinyl acetate, polyvinyl stearate, polyvinyl benzoate, polyvinyl maleate, polyvinylbutyrate, polyallyl phthalate or polyallylmelamine; as well as their copolymers with the olefins mentioned in 1) above.

11. Homopolymers and copolymers of cyclic ethers such as polyalkylene glycols, polyethylene oxide, polypropylene oxide or copolymers thereof with bisglycidyl ethers.

12. Polyacetals such as polyoxymethylene and those polyoxymethylenes which contain ethylene oxide as a comonomer, polyacetals modified with thermoplastic polyurethanes, acrylates or MBS.

13. Polyphenylene oxides and sulfides.

14. Polyurethanes which are derived from polyethers, polyesters or polybutadienes carrying terminal hydroxyl groups on the one hand and aliphatic or aromatic polyisocyanates on the other.

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylenediamine and isophthalic and/or terephthalic acid, with or without an elastomer as modifier, for example poly-2,4,4,-trimethylhexamethylene terephthalamide or poly-m-phenylene isophthalamide; block copolymers of the aforementioned polyamides with polyolefins, olefin copolymers, ionomers or chemically bonded or grafted elastomers; or with polyethers, for example with polyethylene glycol, polypropylene glycol or polytetramethylene glycol; and also polyamides or copolyamides modified with EPDM or ABS, and polyamides condensed during processing (RIM polyamide systems).

16. Polyureas, polyimides and polyamide-imides and polybenzimidazoles.

17. Polyesters derived from dicarboxylic acids and diols and/or from hydroxycarboxylic acids or the corresponding lactones, such as poly-ethylene terephthalate, polybutylene terephthalate, poly-1,4-dimethylolcyclohexane terephthalate, polyhydroxybenzoates as well as block-copolyether esters derived from hydroxyl-terminated polyethers; and also polyesters modified with polycarbonates or MBS.

17a. Polyesters derived from aliphatic dicarboxylic acids and diols and/or oligoethers with the general formula

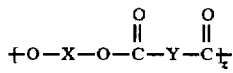

with

X=—(CH$_2$)$_n$— with n=2 to 12 or
X=[—(CH$_2$)$_n$—O—(CH$_2$)$_n$—]$_r$ with n=2 to 4 and r=2 to 10.
Y=—(CH$_2$)$_m$— with m=0 to 12, and
z=5 to 100 and copolymers thereof.

18. Polycarbonates and polyester carbonates.
19. Polysulfones, polyether sulfones and polyether ketones.
20. Polyethers of diglycidyl compounds, including diglycidyl ethers and diols, for example of hisphenol A diglycidyl ether and bisphenol A.
21. Natural polymers such as rubber, and chemically modified homologous derivatives of natural polymers e.g. cellulose acetates, cellulose propionates and cellulose butyrates, or the cellulose ethers, such as methylcellulose (degree of substitution>2.5); as well as rosins and their derivatives.
22. Mixtures of the aforementioned polymers, for example PP/EPDM, Polyamide 6/EPDM or ABS, PVC/EVA, PVS/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPO.

Specific examples of polymers available commercially, and preferred in the practise of the invention include COETHYLENE® SB 0425 and COETHYLENE® SL (polystyrenes); HOSTAFLEX® CM 13 (polyvinyl chloride/vinyl acetate copolymer); ESTERGUM® 8 D and 10 D (colophonium glycerine esters); HOSTALITH® 3067 (polyvinyl chloride); HOSTYREN® 2000, 5000 and 7000 (polystyrenes); solid acrylic resins PLEXIGUM® N 80 (polyethyl acrylate) and M 825 (polymethyl methacrylate); polyvinylacetate copolymers MOWILITH® 20 and 50 with molecular weights 35,000 and 260,000 respectively; colophonium derivatives NEOLYN® 20 and 35 D; polytetrahydrofurans; polyvinylpyrrolidone-vinylacetatecopolymers e.g. LUVISKOL® 28E, 37E and 55E.

The polymer is present in a concentration of preferably 1 to 30%, and more preferably 1 to 10%, by weight in relation to the pesticide.

Other components of the emulsions according to the invention may include emulsifying agents like anionic and/or nonionic dispersants and surfactants, as well as buffers, as described, for example in U.S. Pat. No. 4,938,797.

Suitable anionic dispersants are in general oligomers and polymers, as well as polycondensates, which contain a sufficient number of anionic groups to ensure their water-solubility. Examples of suitable anionic groups are sulfo groups or carboxyl groups; but polymers containing carboxyl groups can only be used in the higher pH range, preferably at a pH higher than 5. The number of anionic groups per polymer molecule is usually at least 60% of the number of monomer units contributing to the structure of the molecule. Oligomers and polymers that contain sulfo groups can be prepared either by polymerising monomers that contain sulfo groups or by sulfonating the appropriate oligomers or polymers. Polymers that contain carboxyl groups can be obtained by saponifying polyacrylates or polymethacrylates, in which case the degree of saponification must be at least 60%. Particularly suitable anionic dispersants are sulfonated polymers and condensates of aromatic sulfonic acids with formaldehyde. Typical examples of such anionic dispersants are:

A. Salts of polystyrenesulfonic acid, in particular the alkali metal, alkaline earth metal and ammonium salts, and the salts of organic amines which can be obtained by polymerising styrenesulfonic acid or salts thereof or by sulfonation of polystyrene and subsequent neutralisation with a suitable base, in which latter case the degree of sulfonation must be at least 60%;

B. Salts of polyvinylsulfonic acid, in particular the alkali metal, alkaline earth metal and ammonium salts, and the salts with organic amines which can be obtained by polymerising vinylsulfonic acid or salts therof;

C. Salts of condensates of naphthalenesulfonic acids, preferably naphthalene-2-sulfonic acid, with formaldehyde, in particular the alkali metal, alkaline earth metal and ammonium salts, and salts thereof with organic amines which can be obtained by sulfonation of naphthalene, condensation of the resultant naphthalenesulfonic acids with formaldehyde, and neutralisation with a suitable base. The molecular weight of these compounds is in the range from about 500 to 6000.

D. Salts of condensates of naphthalenesulfonic acid with phenolsulfonic acid and formaldehyde, in particular the alkali metal, alkaline earth metal and ammonium salts, and salts with organic amines. These products are sulfo group containing polymers with an average molecular weight of 6000 to 8000, in which the monomer units naphthalene and phenol are linked to each other partly through methylene groups and partly through sulfo groups.

E. Salts of ligninsulfonic acid, in particular the sodium, potassium, magnesium, calcium or ammonium salt.

Preferred anionic dispersants are salts of polystyrenesulfonic acid (type A), salts of condensates of naphthalenesulfonic acid with formaldehyde (type C) and, in particular, condensates of naphthalenesulfonic acid with phenolsulfonic acid and formaldehyde (type D).

The condensates of naphthalenesulfonic acid with phenolsulfonic acid and formaldehyde of type D, which are especially preferred anionic dispersants can be prepared by converting naphthalene, at 120° to 130° C., first with concentrated sulfuric acid and/or oleum into naphthalenesulfonic acid, then adding phenol to the reaction mixture, and carrying out further reaction initially at 120° to 130° C. and then removing the water of reaction in vacuo at 150° to 170° C. and condensing the reaction product with formaldehyde after cooling to 90° to 100° C., then neutralising the reaction mixture to pH 6 to 7 and evaporating it to dryness and granulating the residue, affording a water-soluble anionic dispersant (hereinafter referred to as "dispersant A") in granular form with an average molecular weight of 6000 to 8000.

The sulfonation of naphthalene under the above specified conditions yields mainly naphthalene-2-sulfonic acid together with insignificant amounts of naphthalenedisulfonic acid. Upon addition of phenol, this is also sulfonated. However, in this process, in particular when subsequently heating to 150° to 170° C., large mounts of sulfones such as 4,4'-dihydroxydiphenylsulfone and 4-hydroxyphenylnaphthylsulfone are also formed in addition to phenolsulfonic acid. Hence a polymer whose monomer units naphthalene and phenol are linked partly through methylene groups and partly through sulfo groups is formed in the subsequent condensation with formaldehyde. In the preparation of dispersant A, naphthalene, phenol, sulfuric acid, formaldehyde and base may be used in the molar ratio of 1:0.5 to 1:2 to 2.5:0.4 to 0.8:2 to 3. The molar ratio of naphthalene:phenol:sulfuric acid:formaldehyde:base is conveniently 1:0.7:2:0.5:2, with sodium hydroxide being advantageously used as base. The sulfuric acid consists advantageously of mixtures of concentrated sulfuric acid and oleum, with the amount of free $SO_3$ in the oleum being at least equivalent to the amount of water in the concentrated sulfuric acid, so that at least 100% sulfuric acid is formed when mixing concentrated sulfuric acid and oleum. Formaldehyde is conveniently used as aqueous solution, for example as 37% aqueous solution. The separation of the water of reaction by distillation is advantageously effected under a pressure of 10 to 50 mbar.

The aqueous phase of the concentrate according to the invention may also contain emulsion viscosity modifiers.

Suitable emulsion viscosity modifiers and nonionic dispersants are in general water-soluble polymers whose molecular weight is normally in the range from 10,000 to 2,000,000. The average diameter of the emulsion droplets (or particles) can be influenced by the molecular weight of the respective polymer employed. The use of water-soluble polymers of low molecular weight results in a lower viscosity of the emulsion and thus in the formation of larger droplets, whereas the use of water-soluble polymers of high molecular weight leads to a higher viscosity of the emulsion and therefore to the formation of droplets of smaller diameter. Examples of suitable water-soluble polymers are: polyvinyl alcohol, polyvinyl methyl ether, polyvinylpyrrolidone, alkylated polyvinylpyrrolidone, hydroxyethyl cellulose, hydroxypropyl cellulose, methyl cellulose (degree of substitution: 1.5 to 2), hydroxyethylmethyl cellulose, hydroxypropylmethyl cellulose, poly(2-hydroxyethyl) methacrylate, poly[2-(2-hydroxyethoxy)ethyl]methacrylate, polyethylene oxide (polyoxyethylene) and polyallyl alcohol (polyglycidol).

A preferred nonionic dispersant is polyvinyl alcohol. Particularly preferred are polyvinyl alcohols with a viscosity of 4 to 60 mPa·s (measured in 4% aqueous solutions at 20° C.) which have been prepared by saponification of polyvinyl acetate, with the degree of saponification being at least 60%, but preferably 80 to 95%. Suitable products of this kind are those commercially available under the registered trademark MOWIOL®.

Suitable nonionic surfactants are in general nonionic water-soluble polymers having an average molecular weight of below 20,000. Particularly suitable nonionic surfactants of this kind are the products which can be obtained by reaction of ethylene oxide, or by the combined reaction of ethylene oxide and propylene oxide, with fatty alcohols, alkylphenols, fatty acids, fatty acid esters of polyhydroxy compounds, fatty acid amides and fatty amines, where the number of ethylene oxide and propylene oxide units may vary within wide limits. In general, the number of ethylene oxide units or ethylene oxide and propylene oxide units is from 1 to 200, preferably from 5 to 100 and, most preferably, from 8 to 40.

Suitable nonionic surfactants include:

alkylpolyethylene glycol ethers, which are commercially available under the registered trademarks BRIJ® (Atlas Chemical), ETHYLAN® CD and ETHYLAN® D (Diamond Shamrock), GENAPOL® C, GENAPOL® O and GENAPOL® S (Hoechst AG);

alkylphenol polyethylene glycol ethers, available for example under the registered trademarks Antarox (GAF), TRITON® X (Rohm and Haas Co.), ATLOX® 4991 (ICI), ARKOPAL® N (American Hoechst) und ETHYLAN® (Lankro Chem. Ltd);

α-phenethylphenol polyglycol ethers, designated ethoxylated styryl phenols and available for example as DISTY® 125 (Geronazzo) and SOPROPHOR® CY 18 (Rhone Poulenc S.A.);

fatty acid (polyethoxyethyl) esters, available for example under the registered trademarks NONISOL® (Ciba-Geigy) or MRYJ® (ICI);

sorbitan polyethylene glycol ether fatty acid esters, also known as polysorbates and commercially available for example under the registered trademark TWEEN® (ICI);

triglyceride polyethylene glycol ethers, e.g. ethoxylated castor oil, and commercially available under the registered trademark EMULSOGEN® (Hoechst AG);

fatty acid polyethoxyethylamides, available for example under the registered trademarks AMIDOX® (Stephan Chemical Co.) and ETHOMID® (Armak Co.);

N-polyethoxyethylamines, available for example under the registered trademark GENAMIN® (Hoechst AG);

N,N,N'N'-tetra(polyethoxypolypropoxyethyl) ethylenediamines, commercially available under the registered trademarks TERRONIL® and TETRONIC® (BASF Wyandotte Corp.);

alkyl polyethylene glycol/polypropylene glycol ethers, e.g. polyethylene oxide/polypropylene oxide block polymers commercially available under the registered trademark PLURONIC® (BASF Wyandotte Corp.).

Preferred nonionic surfactants are ethylene oxide/ propylene oxide block polymers (PLURONICS®), N,N,N', N'-tetra(polyethoxypolypropoxyethyl)ethylenediamines (TETRONICS®), nonylphenol polyglycol ethers containing 10 to 20 ethylene oxide units, alkyl polyethylene glycol ethers which are derived from fatty alcohols (GENAPOL®) and N-polyethoxyethylamines which are derived from fatty mines (GENAMIN®). Particularly preferred nonionic surfactants are ethylene oxide/propylene oxide block polymers (PLURONICS®).

The dispersing system comprising a dispersing agent and/or a surfactant is present in an amount 0.1 to 5%, preferably 0.3 to 3%, by weight compared with the emulsion components.

The concentrated aqueous emulsion may also contain a thickening agent, e.g. xanthan gum.

It may be advantageous to include in the concentrated aqueous emulsion an antifreezing agent such as 1,2-propyleneglycol, glycerine, ethyleneglycol or freezing point-lowering salts.

A buffer can be present in the emulsions according to the invention in an amount of 0.1 to 6%, preferably 0.1 to 3%, by weight compared to the emulsion components. Suitable buffers are acetic acid (AcOH)/NaOH or AcOH/KOH in the ratio 8:2 to 2:8 by weight with pH 4 to 5, $H_3PO_4$/NaOH or $H_3PO_4$/KOH in the ratio 8:2 to 2:8 with pH 4 to 8, and citric acid/NaOH or citric acid/KOH in the same ratio with pH 4 to 6, or $KH_2PO_4$/Borax in the ratio 8:2 to 2:8 with pH 5.8 to 9.2, or $NH_3$/$NH_4Cl$ in the ratio 2:8 to 8:2 with pH 8 to 11. Mixtures of these buffers are also suitable.

Thus, it is an object of the present invention to provide an aqeous emulsion comprising 1 to 70% (w/w), preferably 5 to 60%, more preferably 10 to 60% of a pesticide or mixture of pesticides, 0.1 to 20% (w/w), preferably 1 to 10% of a polymer or polymer mixture which is more soluble in the organic phase than in the aqeous phase, 0.1 to 5% (w/w) of surfactants and/or dispersants, 0 to 1% (w/w) of a thickening agent, 0 to 30% (w/w) of a hydrophobic solvent, 0 to 6% (w/w) of a buffer and 0 to 10% (w/w) of an antifreezing agent.

Another object of the invention is a process for preparing aqueous emulsions as herein described, wherein a polymer is dissolved in the pesticide, optionally by warming, and this solution is emulsified with an aqueous solution comprising pure water, an anionic or non-ionic emulsifying agent and/or dispersants, a nonionic surfactant and optionally a buffer salt.

The extent to which the polymer has dissolved in the pesticide or pesticide mixture can be determined by measuring the viscosity. If the viscosity increases considerably over that of the pesticide only, one may conclude that the polymer has dissolved. It may be necessary to warm the pesticide to make it more fluid.

The solutions may be emulsified using for example an YSTRAL® T 20 emulsifier with stirring speeds of between 10,000 and 20,000 rpm.

The viscosity of the resulting solutions can be measured using for example a BROOKFIELD® viscosimeter with spindles 2 and 3 at 30 rpm.

The measurement of particle size (diameter) as well as the distribution of particle sizes can be made using for example a CILAS 715 granulometer 715. The median particle diameter (MPD) is preferably 0.5 to 12 µm, more preferably 0.5 to 5 µm, and most preferably 0.5 to 4 µm. It is generally found that fewer than 3% of the particles, preferably <2% and particularly preferred <1% of the particles forming the emulsion according to the invention have a particle diameter in excess of 12 µm.

It may be advantageous to combine the pesticide or mixture of pesticides with a safener.

The emulsion may be combined in any proportion with water before application. Preferred concentrations are 50 to 750 g/l of water, more preferably 300 to 720 g/l. High strength formulations with 500 to 720 g/l can be readily diluted with more aqueous phase to low strength formulations (i.e. 10 to 400 g/l) without change in particle size.

Further aspects of the invention include a method of preventing or combatting infestation of plant species or animals by pests, and regulating plant growth by diluting an amount of emulsion concentrate with pure water and applying to the plant, tree, animal or locus as desired.

The emulsion can be stored conveniently in a container from which it is poured or into which water is poured prior to application.

The advantages of the emulsions presently described are as follows:

a) they contain little or no organic solvent;

b) they are storage-stable for a period in excess of two years;

c) simple handling is made possible for users because dilution is made with water for preparation of application mixtures;

d) there is negligible change in particle size during storage or on dilution.

Furthermore, the small amount or absence of organic solvent reduces the risk of inflammation, toxicity to animals and provides an environmentally more attractive delivery system.

In the following Examples which illustrate the invention in more detail, the registered trademarks and other designations that are not self-evident denote the following products:

Anionic Dispersant

Dispersant A: sodium salt of a condensate of naphthalenesulfonic acid with phenolsulfonic acid and formaldehyde, prepared according to Example 1.

Nonionic Dispersants

MOWIOL® 18-88: polyvinyl alcohol with a viscosity of 18 mPa·s (measured in a 4% aqueous solution at 20° C.), prepared by saponification of polyvinyl acetate (degree of saponification: 88%), supplier Hoechst AG.

ANTARON® P 904 alkylated polyvinylpyrrolidone, supplier GAF.

Nonionic Surfactant

PLURONIC® F-108: ethylene oxide/propylene oxide block polymer of the formula $(EO)_x$—$(PO)_y$—$(EO)_z$, with mol wt of c. 16,000 and an ethylene oxide content of 80%, supplier BASF Wyandotte Corp.

EXAMPLE 1

Preparation of Dispersing Agent A

Starting materials:

288 g (2.25 moles) naphthalene, 144 g (1.53 moles) phenol, 440 g (4.48 moles) 100% sulfuric acid, 78.5 g (0.97 mole) 37% aqueous formaldehyde, 370 g (4.4 moles) 48% aqueous NaOH.

The naphthalene is melted in a stirred reactor and after addition of sulfuric acid, the melt is heated for 4 hours to 120° to 125° C. The phenol is then added and the temperature is kept at 120° to 125° C. for a further hour. The reaction vessel is subsequently evacuated to a pressure of 15 mbar and the temperature is increased slowly to 160° C. and kept there for 3 hours while the water of reaction is distilled off. The reaction mixture is cooled to 105° to 110° C. and homogenised by stirring. The batch is then cooled to 90° C. by cautious addition of 200 g ice, while maintaining the homogeneity of the mixture by continual stirring. The formaldehyde solution is then added at 90° to 95° C. over 1 hour and stirred for 3 hours at 95° C. A sample of the reaction mixture then forms with water a clear 5% solution and no longer smells of formaldehyde. The reaction mixture is then cooled to 80° C. by addition of 60 g of ice and 60 g water. After addition of a further 180 ml water, the reaction mixture is neutralised with about 230 to 250 ml 48% NaOH solution at 80° C. The pH of a 10% solution of a sample of the reaction mixture is about 6.5. The reaction mixture is then evaporated to dryness and the residue is granulated, affording 900 g of Dispersant A in the form of water-soluble granules.

The following examples illustrate the use of polymers to increase the viscosity of the liquid pesticide active ingredient (AI) and thus improve the stability of oil in water emulsions formed with such AI/polymer mixtures:

EXAMPLE 2

2a) O,O-diethyl O-2-isopropyl-6-methylpyrimidin-4-yl phosphorothioate without polymer and without buffer: 161.8 g O,O-diethyl O-2-isopropyl-6-methylpyrimidin-4-yl phosphorothioate (technical quality 92.7%; viscosity 14 mPa-s) are emulsified in a solution of 6 g MOWIOL® 18-88 and 15 g 1,2-propyleneglycol in 117.2 g water by means of a high shear stirrer at 10,000 rpm for 5 minutes. The viscosity of the resulting emulsion is 800 to 900 mPa-s (Brookfield, spindle 2, 30 rpm). The median particle diameter (MPD) is 2.0 to 2.5 µm (CILAS granulometer). The particle diameter distribution indicates about 38% of the particles>12 µm.

2b) As in 2a) but with polymer: 8.5 g COETHYLENE® SB 0425 (a powder of polystyrene with an average molecular weight $M_w$ of 200,000 to 300,000) are dissolved in 161.8 g O,O-diethyl O-2-isopropyl-6-methylpyrimidin-4-yl phosphorothioate which are emulsified as in 2a) above. The resulting viscosity is 120 to 200 mPa·s. The amount of water for emulsification is reduced by 8.5 g. The resulting emulsion has a viscosity of 800 to 900 mPa-s, with none of the particles greater than 12 µm.

EXAMPLE 3

3a) Polymer absent: 2.1 g dispersing agent A, 2.1 g PLURONIC® F 108, 2 g xanthan gum, 0.2 g formaldehyde, 2.0 g phosphoric acid (75%) and 3.8 g NaOH (30%) are dissolved in 71.1 g water. This solution forms the continuous aqueous phase. 128 g O,O-diethyl O-2-isopropyl-6-methylpyrimidin-4-yl phosphorothioate (95%) are emulsified in the aqueous phase under high shear stirring (YSTRAL T 20, 12,000 rpm) and stirring is continued for 3 minutes.

The resulting emulsion is coarse and has a median particle diameter of 10.9 µm. The particle diameter distribution is broad with 14%>12 µm. The emulsion is of low viscosity (80 mPa·s) and exhibits phase separation within hours to days.

3b) Polymer present: the aqueous solution is prepared as above using 61.6 g water only. In a second beaker 6 g COETHYLENE® SB 0425 are dissolved in 128 g O,O-diethyl O-2-isopropyl-6-methylpyrimidin-4-yl phosphorothioate (95%). The solutions are combined and emulsified as described in 3a above.

The resulting emulsion is fine and has a median particle diameter of 2 to 4 µm. No particles are detected with diameter>12 µm. The viscosity is higher at 800 to 1600 mPa·s. The emulsion is storage stable at ambient and elevated temperatures. The viscosity is found to remain at 600 to 1200 mPa·s and median particle diameter is 2 to 4 µm after 3 months at room temperature (RT) and 45° C. respectively.

Preparation of Sprays

The emulsion of 3a) does not form a sprayable liquid on dilution, even immediately after preparation. The emulsion from 3b) exhibits a stable emulsion both in CIPAC A and CIPAC D water (standard water qualities as described in the CIPAC Handbook). After 1 hour, only traces of settling can be observed and re-suspensibility is readily achieved even after 24 hours.

3c) In a beaker 8 g of dispersing agent A, 8 g of PLURONIC F-108, 1.6 g of xanthan gum and 1.6 g of formaldehyde are dissolved in 380 g of deionized water. In a second beaker 19 g of Coethylene SB 0425 are dissolved in a mixture of 336.8 g of technical O,O-diethyl O-2-isopropyl-6-methylpyrimidin-4-yl phosphorothioate (95.1%) and 41.6% technical (RS)-α-cyano-3-phenoxybenzyl(1RS)-cis-trans-3-(2,2-dichlorovinyl)-1,1-dimethyl-cyclopropanecarboxylate (96.1%) at 70° C. This second mixture is emulsified with a YSTRAL-T-20 mixer at 14'000 rpm into the above aqueous mixture for 5 minutes resulting in an emulsion with MPD=2 µm and a viscosity of 700 to 1000 mPa·s.

EXAMPLE 4

4a) The following mixture without polymer is emulsified as in 2a)

6.0 g MOWIOL® 18-88

15.0 g 1,2-propyleneglycol 159.1 g O-5-chloro-1-isopropyl-1H-1,2,4-triazol-3-yl O,O-diethyl phosphorothioate technical (94.3%)

120.0 g water

Viscosity: 350 mPa·s

MPD: 2.1 µm.

Proportion>12 µm: 24%.

4b) The following mixture with polymer is emulsified as in 2b)

7.5 g COETHYLENE® SB 0425

159.1 g O-5-chloro-1-isopropyl-1H-1,2,4-triazol-3-yl O,O-diethyl phosphorothioate technical grade (The mixture of the above two components has a viscosity of 140 to 240 mPa·s.)

6.0 g MOWIOL® 18-88

15.0 g 1,2-propyleneglycol 112.5 g water

Viscosity: 490 mPa·s

MPD: 2.2 µm

Proportion>6 µm: 0%.

Storage Stability

After 3 months at −10° C./RT/35° C. respectively samples from 4a) show strong settling with formation of a clear top layer. No settling and clear layer formation are observed in samples from 4b) under the same storage conditions.

EXAMPLE 5

The following mixture with polymer is emulsified using an YSTRAL T 20 emulsifier for 5 minutes at 10,000 rpm.

6.4 g COETHYLENE® SB 0425

128.0 g O-5-chloro-1-isopropyl-1H-1,2,4-triazol-3-yl O,O-diethyl phosphorothioate technical grade (93.7%)

2.0 g MOWIOL® 18-88

63.6 g water

MPD: 1–2 µm

Proportion>12 µm: <1%.

EXAMPLE 6

The following mixture with polymer is emulsified using an YSTRAL T 20 emulsifier for 5 minutes at 10,000 rpm.

0.9 g COETHYLENE® SB 0425

17.1 g O-5-chloro-1-isopropyl-1H-1,2,4-triazol-3-yl O,O-diethyl phosphorothioate technical grade (93.7%)

29.0 g MOWIOL® 18-88

15.0 g 1,2-propyleneglycol 250.0 g water
MPD: 1–2 μm
Proportion>12 μm: <2%.
Viscosity: 300 to 400 mPa·s

EXAMPLE 7

The following mixture with polymer is emulsified using an YSTRAL T 20 emulsifier for 5 minutes at 10,000 rpm.

8.8 g COETHYLENE® SB 0425

166.7 g O-5-chloro-1-isopropyl-1H-1,2,4-triazol-3-yl O,O-diethyl phosphorothioate technical grade (93.7%)

(The mixture of the above two components only has a viscosity of 380 mPa·s).

6.0 g MOWIOL® 18-88
15.0 g 1,2-propyleneglycol
103.5 g water
MPD: 1.5–2.5 μm
Proportion>12 μm: <1%.
Viscosity: 1000 to 1400 mPa·s

EXAMPLE 8

The following mixture with polymer is emulsified using an YSTRAL T 20 emulsifier for 5 minutes at 10,000 rpm.

5.4 g COETHYLENE® SB 0425

107.4 g 2-chloro-1-(2,4-dichloro-phenyl)vinyl diethyl phosphate (technical 93.1%)

(The mixture of the above two components has a viscosity of 600 mPa·s).

65.6 g Acetate-buffer solution (10%) (AcOH/NaOAc 2:8)
3.0 g MOWIOL® 18-88
10.0 g 1,2-propyleneglycol
31.6 g water
MPD: 1.5–2.5 μm
Proportion>12 μm: <2%.
Viscosity: 80 to 300 mPa·s

EXAMPLE 9

9a) No polymer present: 2.0 g MOWIOL 18-88 and 10.0 g 1,2-propyleneglycol are dissolved in 61.2 g water. 149.2 g technical grade 2-chloro-6'-ethyl-N-(2-methoxy-1-methylethyl)acet-o-toluidide (96.5%) are emulsified with this solution in an YSTRAL T 20 at 10,000 rpm for 5 minutes. The MPD is 7 to 8 μm and 15 to 25% of the particles are larger than 12 μm. The initial viscosity of this emulsion is 2,500 to 3,000 mPa·s but drops rapidly to 1000 to 1500 mPa·s.

9b) Polymer present: 2.0 g MOWIOL 18-88 and 10.0 g 1,2-propyleneglycol are dissolved in 56.7 g water. In a second beaker 4.5 g Coethylene SB 0425 are dissolved in 149.2 g technical grade 2-chloro-6'-ethyl-N-(2-methoxy-1-methylethyl)acet-o-toluidide (95.7%) and the viscosity of this solution is 300 to 500 mPa·s. The two solutions are emulsified using an YSTRAL T 20 at 10,000 rpm for 5 minutes. The MPD is 1.5 to 2.5 μm and fewer than 1% of the particles are larger than 12 μm.

The viscosity of this emulsion is 300 to 500 mPa·s and remains constant.

9c) Emulsion is prepared as for 9b) but the MOWIOL® is replaced by ANTARON® P 904.

MPD: 1.5 to 2.5 μm
Proportion>12 μm: fewer than 1%.
Viscosity: 1200 to 1500 mPa·s.

EXAMPLE 10

10a) Polymer absent: 6.0 g MOWIOL 18-88 and 15.0 g 1,2-propyleneglycol are dissolved in 124.4 g water. 154.6 g 2-chloro-6'-ethyl-N-(2-methoxy-1-methylethyl)acet-o-toluidide (97%) are emulsified by means of a high shear mixer (YSTRAL T 20) at 10,000 rpm for 5 minutes. The resulting emulsion has a viscosity of 300 to 400 mPa·s. The MPD is 5.5 which increases within 4 weeks to 25 μm. After 3 to 6 months phase separation takes place. Variation in shear intensity by modifying the stirring speed in the range 5,000 to 15,000 rpm does not improve storage stability.

10b) Polymer absent: an emulsion is prepared as in 10a) but 3 g dispersing agent A and 3 g PLURONIC® F 108 are used instead of MOWIOL® 18-88. The resulting emulsion has a viscosity of 20 to 50 mPa·s, and an MPD of 9 to 10 μm which increases within 4 weeks to 35 μm. Phase separation takes place as above within 3 to 6 months.

10c) Polymer present (COETHYLENE® SB 0425): an aqueous solution is prepared as in 10a) except that only 116.3 g water are used. In a second beaker 8.1 g COETHYLENE® SB 0425 are dissolved in 154.6 g 2-chloro-6'-ethyl-N-(2-methoxy-1-methylethyl)acet-o-toluidide (97%) resulting in a viscosity of 200 to 300 mPa·s. The solutions are emulsified together as in 10a) and the following properties are observed:

Viscosity: 350 to 450 mPa·s.
MPD: 1.5 to 2.0 μm
no particles>12 μm.

After 6 months at RT the MPD and particle diameter distribution remain unchanged.

EXAMPLE 11

Polymer present: ESTERGUM® 8 D. An emulsion is prepared as 10c) above but 8.1 g ESTERGUM® 8 D are used instead of COETHYLENE® SB 0425.

MPD: 0.5 to 1.0 μm.
Viscosity: 500 to 600 mPa·s.

After 6 months at RT the MPD, particle diameter distribution and viscosity are unchanged.

EXAMPLE 12

Higher polymer content present: 2.8 g MOWIOL® 18-88 and 7 g 1,2-propyleneglycol are dissolved in 49 g water. In a second beaker 14.5 g COETHYLENE® SB 0425 are dissolved in 72.3 g 2-chloro-6'-ethyl-N-(2-methoxy-1-methylethyl)acet-o-toluidide (96%). The two solutions are emulsified together at 50° C. with a high shear stirrer (YSTRAL T 20, 15,000 rpm) for 3 minutes. The following properties are found:

Viscosity: 360 mPa·s.
MPD: 2 to 3 μm.
No particles are detected>12 μm.

EXAMPLES 13–22

Emulsions with similar properties to those in Example 12 above are obtained with the polymer present in an amount of one of the following:

13) 20% MOWILITH® 20
14) 20% PLEXIGUM® P 28
15) 25% ESTERGUM® 10 D
16) 10% PLEXIGUM® N 80
17) 10% MOWILITH® 50
18) 15% COETHYLENE® SL 19) 10% HOSTYREN® 5.000
20) 10% HOSTAFLEX® CM 113
21) 15% HOSTALITH® 3067
22) 8% PLEXIGUM® M 825

In the above examples 13 to 22 the viscosities of the AI/polymer mixtures are very high. Therefore preparation of the oil-in-water emulsion has to be undertaken at elevated temperatures to make the AI/polymer mixtures less viscous. Lower amounts of polymer are feasible, too.

EXAMPLE 23

23a) 2 g dispersing agent A, 2 g PLURONIC® F 108 and 10 g 1,2-propyleneglycol are dissolved in 74.3 g water. In a second beaker 2.2 g COETHYLENE® SB 0425 polymer are dissolved in 109.5 g (±)-1[2-(2,4-dichlorophenyl)-4-propyl-1,3-dioxolan-2-ylmethyl]-1H-1,2,4-triazole (technical 91.3%). The latter mixture has a viscosity of 700 to 1000 mPa·s at about 50° C. The mixture is emulsified in the aqueous phase using an YSTRAL T 20 at 15,000 rpm for 5 minutes. The following properties are observed:

MPD: 3 to 4 µm.

No particles are observed>12 µm.

No phase separation or sedimentation are observed during storage.

23b) An emulsion is prepared as in 22a) without COETHYLENE® SB 0425 with MPD 7 to 10 µm and at least 25% of the particles larger than 12 µm. The emulsion separates to a degree of 30% within a few days.

23c) In a beaker 1.6 g of dispersing agent A, 1.6 g of PLURONIC F-108, 0.2 g of xanthan gum, 0.2 g of formaldehyde and 1.0 g of sodium hydroxide (30%) are dissolved in 76 g of deionized water. The mixture has a pH of 10 to 12. In a second beaker 4 g of Coethylene SB 0425 are dissolved in a mixture of 64 g of (RS)-1-[3-(4-tert-butylphenyl)-2-methylpropyl]piperidine (technical 96.6%) and 20 g of (±)-1[2-(2,4-dichlorophenyl)-4-propyl-1,3-dioxolan-2-ylmethyl]-1H-1,2,4-triazole (technical 91.3%) at 70° C. This second mixture is emulsified into the above described aqueous mixture with a YSTRAL-T-20 mixer at 14'000 rpm for 5 minutes resulting in an emulsion with a MPD=2 to 3 µm and a viscosity of 200 to 400 mPa·s.

EXAMPLE 24

1.6 g dispersing agent A and 1.6 g PLURONIC® F 108 are dissolved in 83.6 g water. In a second beaker 4.5 g COETHYLENE SB 0425 polymer are dissolved in 84.7 g 2',4'-dichloro-2-(3-pyridyl)acetophenone O-methyloxime. The solutions are emulsified together using an YSTRAL T 20 at 15,000 rpm for 5 minutes. The resulting emulsion has a viscosity of 200 to 300 mPa·s and MPD of 2 to 3 µm.

EXAMPLE 25

1.0 g dispersing agent A and 1.0 g PLURONIC® F 108 are dissolved in 42.4 g water. In a second beaker 2.6 g COETHYLENE® SB 0425 polymer are dissolved in 53.1 g technical grade cis,trans-(±)-2-ethyl-5-(4-phenoxy-phenoxymethyl)-1,3-dioxolane (94.1%). The viscosity of this solution is 400 to 600 mPa·s. This solution is emulsified in the aqueous phase by means of a high shear mixer (YSTRAL T20) at 18,000 rpm for 3 minutes. The resulting emulsion has a viscosity of 300 to 500 mPa·s and a median particle size of 1.6 to 2.2 µm.

EXAMPLE 26

As in Example 25 but 1.1 g COETHYLENE® SB 0425 polymer are used. The viscosity of the pesticide/polymer solution is 100 to 200 mPa·s. The resulting emulsion has similar properties i.e. low to moderate viscosity and MPD ca. 2 µm.

EXAMPLE 27

In a beaker 1.6 g of OROTAN SN, 1.6 g of PLURONIC F-108, 0.3 g of PROXEL BD, 0.1 g of sodium hydroxide (30%) are dissolved in 47.8 g of deionized water. In a second beaker 5 g of Coethylene SB 0425 are dissolved in 100 g of (RS)-1-[3-(4-tert-butylphenyl)-2-methylpropyl]piperidine (technical 96%) at 70° C. This mixture is emulsified in the aqueous phase with a YSTRAL-T-20 mixer at 14'000 rpm for 5 minutes resulting in an emulsion with a MPD=3 to 5 µm and a viscosity of 1'500 to 2'000 mPa·s.

EXAMPLE 28

In a beaker 1 g of OROTAN SN (^TAMOL SN), 1 g of PLURONIC F-108, 5 g of 1,2-propylenglycole and 0.2 g of xanthan gum are dissolved in 32.5 g of deionized water. In a second beaker 1 g of Coethylene SB 0425 is dissolved in a mixture of 41.7 g of glycerin triacetate and 20.5 g 1-(2,4-dichloro-β-propylphenethyl)-1H-1,2,4-triazole (technical 97.6%). The mixture is emulsified in the aqueous phase with a YSTRAL-T-20 mixer at 14'000 rpm for 5 minutes resulting in an emulsion with a MPD=2 µm and a viscosity of 700 to 1'000 mPa·s.

APPLICATION EXAMPLES

Field Tests

The efficacy of the inventive formulations is illustrated below. Compared are the formulation as prepared by example 3b (A) with the corresponding emulsifiable concentrate (B). In each example the control indicates the number of aphids. The results for each formulation show the number of aphids as a percentage of the contol (% C).

EXAMPLE F.1

Crop: Apple (golden delicious)

Pest: *Aphis pomi*

| g AI/hl | Days after treatment | | | | |
|---|---|---|---|---|---|
| | 0 | 2 | 7 | 15 | 20 |
| A 50 | | 74 | 87 | 75 | 85 % C |
| B 50 | | 97 | 97 | 80 | 83 % C |
| Control: number of aphids | 620 | 317 | 314 | 146 | 269 |

EXAMPLE F.2

Crop: Apple (golden delicious)

Pest: *Aphis pomi*

| g AI/hl | Days after treatment | | | | |
|---|---|---|---|---|---|
| | 0 | 2 | 7 | 13 | 20 |
| A 50 | | 95 | 100 | 96 | 86 % C |
| B 50 | | 91 | 94 | 90 | 89 % C |
| Control: no. of aphids | 860 | 1260 | 455 | 485 | 741 |

EXAMPLE F.3

Crop: Field bean
Pest: *Aphis fabae*

| g AI/hl | Days after treatment | | | | | |
|---|---|---|---|---|---|---|
| | 0 | 2 | 6 | 13 | 20 | |
| A 600 | | 100 | 100 | 99 | 95 | % C |
| B 600 | | 100 | 100 | 100 | 98 | % C |
| Control: no. of aphids | 920 | 3220 | 2071 | 2951 | 3750 | |

I claim:

1. A two-phase aqueous emulsion having an organic phase including a substantially hydrophobic pesticide or mixture of pesticides which are liquid or dissolved in a hydrophobic solvent, and an aqueous phase including a surfactant and/or dispersing agent dissolved in water, which comprises:

1 to 30% by weight in relation to said pesticide or mixture of pesticides of a polymer or polymer mixture having a polymer molecular weight, as measured by viscosity or light scattering, of between 10,000 and 1,000,000 daltons, which polymer or polymer mixture is dissolved in the organic phase and substantially insoluble in the aqueous phase, wherein the polymer or polymer mixture is substantially insoluble in water, stable to hydrolysis, and dissolves in said pesticide or mixture of pesticides, and wherein the polymer or polymer mixture is selected from a polymer class consisting of polyolefins, hydrocarbon resins, polystyrenes, polyacrylates, poly methacrylates, polyacrylamides, polyacrylonitriles, polymers of cyclic ethers, polyacetals, poly phenylenes, polyurethanes, polyamides, polyureas, polyimides, polyesters, poly carbonates, polysulfones, rubber or copolymers thereof, and wherein a) the substantially hydrophobic pesticide is at least one compound selected from the group consisting of:

O,O-diethyl O-2-isopropyl-6-methylpyrimidin-4-yl phosphorothioate,

O-5-chloro-1-isopropyl-1H-1,2,4-triazol-3-yl O,O-diethyl phosphorothioate, 2-chloro-1-(2,4-dichloro-phenyl)vinyl diethyl phosphate, 2-chloro-6'-ethyl-N-(2-methoxy-1-methylethyl)acet-o-toluidide, (±)-1[2-(2,4-dichlorophenyl)-4-propyl-1,3-dioxolan-2-ylmethyl]-1H-1,2,4-triazole, 2',4'-dichloro-2-(3-pyridyl)acetophenone O-methyloxime, cis,trans-(±)-2-ethyl-5-(4-phenoxy-phenoxymethyl)-1,3-dioxolane, (RS)-1-[3-(4-tert-butylphenyl)-2-methylpropyl]piperidine, 1-(2,4-dichloro-b-propylphenethyl)-1H-1,2,4-triazole, and (RS)-a-cyano-3-phenoxybenzyl(1RS)-cis-trans-3-(2,2-dichloro vinyl)-1,1-dimethyl-cyclopropanecarboxylate, and b) the weight ratio compared to the total two-phase aqueous emulsion is 1–70% for the pesticide or mixture of pesticides, 0.1–20% for the polymer or polymer mixture, and 0.1–5% for the surfactant and/or dispersing agent.

2. A process for preparing two-phase aqueous emulsions having an organic phase including a substantially hydrophobic pesticide or mixture of pesticides which are liquid or dissolved in a hydrophobic solvent, and an aqueous phase including a surfactant and/or dispersing agent dissolved in water, said two-phase aqueous emulsions comprising:

1 to 30% by weight in relation to said pesticide or mixture of pesticides of a polymer or polymer mixture having a polymer molecular weight, as measured by viscosity or light scattering, of between 10,000 and 1,000,000 daltons, which polymer or polymer mixture is dissolved in the organic phase and substantially insoluble in the aqueous phase, wherein the polymer or polymer mixture is substantially insoluble in water, stable to hydrolysis, and dissolves in said pesticide or mixture of pesticides, and wherein the polymer or polymer mixture is selected from a polymer class consisting of polyolefins, hydrocarbon resins, polystyrenes, polyacrylates, poly methacrylates, polyacrylamides, polyacrylonitriles, polymers of cyclic ethers, polyacetals, poly phenylenes, polyurethanes, polyamides, polyureas, polyimides, polyesters, poly carbonates, polysulfones, rubber or copolymers thereof, and wherein a) the substantially hydrophobic pesticide is at least one compound selected from the group consisting of:

O,O-diethyl O-2-isopropyl-6-methylpyrimidin-4-yl phosphorothioate,

O-5-chloro-1-isopropyl-1 H-1,2,4-triazol-3-yl O,O-diethyl phosphorothioate, 2-chloro-1-(2,4-dichloro-phenyl)vinyl diethyl phosphate, 2-chloro-6'-ethyl-N-(2-methoxy-1-methylethyl)acet-o-toluidide, (±)-1[2-(2,4-dichlorophenyl)-4-propyl-1,3-dioxolan-2-ylmethyl]-1H-1,2,4-triazole, 2',4'-dichloro-2-(3-pyridyl)acetophenone O-methyloxime, cis,trans-(±)-2-ethyl-5-(4-phenoxy-phenoxymethyl)-1,3-dioxolane, (RS)-1-[3-(4-tert-butylphenyl)-2-methylpropyl]piperidine, 1-(2,4-dichloro-p-propylphenethyl)-1H-1,2,4-triazole, and (RS)-α-cyano-3-phenoxybenzyl(1RS)-cis-trans-3-(2,2-dichloro vinyl)-1,1-dimethyl-cyclopropanecarboxylate, and b) the weight ratio compared to the total two-phase aqueous emulsion is 1–70% for the pesticide or mixture of pesticides, 0.1–20% for the polymer or polymer mixture, and 0.1–5% for the surfactant and/or dispersing agent, said process comprising dissolving the polymer or polymer mixture in the organic phase to form a mixture, warming the mixture if necessary, and emulsifying the mixture with high shear mixing of between 10,000 and 20,000 rpm in the aqueous solution.

3. A method of preventing or combating infestation of plant species or animals by pests, and regulating plant growth, said method comprising applying to a plant, tree, animal or other locus a composition including a two-phase aqueous emulsion concentrate diluted with water, said two-phase aqueous emulsion concentrate having an organic phase including a substantially hydrophobic pesticide or mixture of pesticides which are liquid or dissolved in a hydrophobic solvent, and an aqueous phase including a surfactant and/or dispersing agent dissolved in water, said two-phase aqueous emulsion concentrate comprising:

1 to 30% by weight in relation to said pesticide or mixture of pesticides of a polymer or polymer mixture having a polymer molecular weight, as measured by viscosity or light scattering, of between 10,000 and 1,000,000 daltons, which polymer or polymer mixture is dissolved in the organic phase and substantially insoluble in the aqueous phase, wherein fie polymer or polymer mixture is substantially insoluble in water, stable to hydrolysis, and dissolves in said pesticide or mixture of pesticides, end wherein the polymer or polymer mixture is selected from a polymer class consisting of polyolefins, hydrocarbon resins, polystyrenes, polyacrylates, poly methacrylates, polyacrylamides, polyacrylonitriles, polymers of cyclic ethers, polyacetals, poly phenylenes, polyurethanes, polyamides, polyureas, polyimides, polyesters, poly carbonates, polysulfones, rubber or copolymers thereof, and wherein a) the substantially hydrophobic pesticide is at least one compound selected from the group consisting of:

O,O-diethyl O-2-isopropyl-6-methylpyrimidin-4-yl phosphorothioate,

O-5-chloro-1-isopropyl-1H-1,2,4-triazol-3-yl O,O-diethyl phosphorothioate, 2-chloro-1-(2,4-dichloro-phenyl)vinyl diethyl phosphate, 2-chloro-6'-ethyl-N-(2-methoxy-1-methylethyl)acet-o-toluidide, (±)-1[2-(2,4-dichlorophenyl)-4-propyl-1,3-dioxolan-2-ylmethyl]-1H-1,2,4-triazole, 2',4'-dichloro-2-(3-pyridyl)acetophenone O-methyloxime, cis,trans-(±)-2-ethyl-5-(4-phenoxy-phenoxymethyl)-1,3-dioxolane, (RS)-1-[3-(4-tert-butylphenyl)-2-methylpropyl]piperidine, 1-(2,4-dichloro-β-propylphenethyl)-1H-1,2,4-triazole, and (RS)-α-cyano-3-phenoxybenzyl(1RS)-cis-trans-3-(2,2-dichloro vinyl)-1,1-dimethyl-cyclopropanecarboxylate, b) the weight ratio compared to the total two-phase aqueous emulsion concentrate is 1–70% for the pesticide or mixture of pesticides, 0.1–20% for the polymer or polymer mixture, and 0.1–5% for the surfactant and/or dispersing agent.

4. An aqueous spray emulsion containing a pesticidally effective amount of a two-phase aqueous emulsion concentrate diluted in water, said two-phase aqueous emulsion concentrate having an organic phase including a substantially hydrophobic pesticide or mixture of pesticides which are liquid or dissolved in a hydrophobic solvent, and an aqueous phase including a surfactant and/or dispersing agent dissolved in water, which two-phase aqueous emulsion concentrate comprises:

1 to 30% by weight in relation to said pesticide or mixture of pesticides of a polymer or polymer mixture having a polymer molecular weight, as measured by viscosity or light scattering, of between 10,000 and 1,000,000 daltons, which polymer or polymer mixture is dissolved in the organic phase and substantially insoluble in the aqueous phase, wherein the polymer or polymer mixture is substantially insoluble in water, stable to hydrolysis, and dissolves in said pesticide or mixture of pesticides, and wherein the polymer or polymer mixture is selected from a polymer class consisting of polyolefins, hydrocarbon resins, polystyrenes, polyacrylates, poly methacrylates, polyacrylamides, polyacrylonitriles, polymers of cyclic ethers, polyacetals, poly phenylenes, polyurethanes, polyamides, polyureas, polyimides, polyesters, poly carbonates, polysulfones, rubber or copolymers thereof, and wherein a) the substantially hydrophobic pesticide is at least one compound selected from the group consisting of:

O,O-diethyl O-2-isopropyl-6-methylpyrimidin-4-yl phosphorothioate,

O-5-chloro-1-isopropyl-1H-1,2,4-triazol-3-yl O,O-diethyl phosphorothioate, 2-chloro-1-(2,4-dichloro-phenyl)vinyl diethyl phosphate, 2-chloro-6'-ethyl-N-(2-methoxy-1-methylethyl)acet-o-toluidide, (±)-1[2-(2,4-dichlorophenyl)-4-propyl-1,3-dioxolan-2-ylmethyl]-1H-1,2,4-triazole, 2',4'-dichloro-2-(3-pyridyl)acetophenone O-methyloxime, cis,trans-(±)-2-ethyl-5-(4-phenoxy-phenoxymethyl)-1,3-dioxolane, (RS)-1-[3-(4-tert-butylphenyl)-2-methylpropyl]piperidine, 1-(2,4-dichloro-p-propylphenethyl)-1H-1,2,4-triazole, and (RS)-α-cyano-3-phenoxybenzyl(1RS)-cis-trans-3-(2,2-dichloro vinyl)-1,1-dimethyl-cyclopropanecarboxylate, b) the weight ratio compared to the total two-phase aqueous emulsion concentrate is 1–70% for the pesticide or mixture of pesticides, 0.1–20% for the polymer or polymer mixture, and 0.1–5% for the surfactant and/or dispersing agent.

5. An emulsion according to claim 1, wherein the pesticide is O,O-diethyl O-2-isopropyl-6-methylpyrimidin-4-yl phosphorothioate.

6. An emulsion according to claim 1, wherein the pesticide is 1-(2,4-dichloro-β-propylphenethyl)-1H-1,2,4-triazole.

7. An emulsion according to claim 1, wherein the pesticide is liquid at ambient temperature or can be liquefied by warming, and is substantially insoluble in water.

8. An emulsion according to claim 1, wherein the pesticide is cis,trans-(±)-2-ethyl-5-(4-phenoxy-phenoxymethyl)-1,3-dioxolane.

9. An emulsion according to claim 1, wherein the polymer molecular weight is between 30,000 and 300,000 daltons.

10. An emulsion according to claim 1, wherein the polymer is present in a concentration of 1 to 10% by weight in relation to the pesticide.

11. An emulsion according to claim 1, wherein the dispersing agent and/or surfactant is present in an mount 0.3 to 3% by weight compared with the emulsion components.

12. An emulsion according to claim 1, wherein the dispersing agent is an anionic dispersant comprising an alkali, alkaline earth or ammonium salt of sulfonated naphthalene/formaldehyde condensate or a salt of sulfonated polystyrene.

13. An emulsion according to claim 1, wherein the dispersing agent is the sodium, potassium, magnesium, calcium or ammonium salt of ligninsulfonic acid.

14. An emulsion according to claim 1, wherein the dispersing agent is a nonionic dispersant comprising a water-soluble polymer whose molecular weight is in the range from 10,000 to 2,000,000 daltons.

15. An emulsion according to claim 14, wherein the nonionic dispersant is a polyvinyl alcohol, polyvinyl methyl ether, polyvinylpyrrolidone, alkylated polyvinylpyrrolidone, hydroxyethyl cellulose, hydroxypropyl cellulose, methyl cellulose (degree of substitution: 1.5–2), hydroxyethylmethyl cellulose, hydroxypropylmethyl cellulose, poly(2-hydroxyethyl)methacrylate, poly[2-(2-hydroxyethoxy)ethyl]methacrylate, polyethylene oxide (polyoxyethylene) or polyallyl alcohol (polyglycidol).

16. An emulsion according to claim 15, wherein the nonionic dispersant is a polyvinyl alcohol with a viscosity of 4–60 mPa·s, prepared by saponification of polyvinyl acetate, with the degree of saponification being at least 60%.

17. An emulsion according to claim 16, wherein the degree of saponification is 80–95%.

18. An emulsion according to claim 1, wherein the dispersing system comprises a non-ionic surfactant which is a nonionic wafer-soluble polymer having an average molecular weight of below 20,000.

19. An emulsion according to claim 18, wherein the nonionic surfactant is a product obtained by reaction of ethylene oxide, or by the combined reaction of ethylene oxide and propylene oxide, with fatty alcohols, alkylphenols, fatty acids, fatty acid esters of polyhydroxy compounds, fatty acid amides and fatty amines, where the number of ethylene oxide units or ethylene oxide and propylene oxide units may vary from 1–200.

20. An emulsion according to claim 19, wherein the number of ethylene oxide units or ethylene oxide and propylene oxide units may vary from 5–100.

21. An emulsion according to claim 20, wherein the number of ethylene oxide units or ethylene oxide and propylene oxide units may vary from 8–40.

22. An emulsion according to claim 1, wherein a buffer is additionally present in an mount 0.1 to 6% by weight compared to the emulsion components.

23. An emulsion according to claim 22, wherein the buffer is present in an amount 0.1 to 3% by weight compared to the emulsion components.

24. An emulsion according to claim 22, wherein the buffer is acetic acid (AcOH)/NaOH or AcOH/KOH in the ratio 8:2 to 2:8 by weight with pH 4 to 5, $H_3PO_4$/NaOH or $H_3PO_4$/KOH in the ratio 8:2 to 2:8 with pH 4 to 8, or citric acid/NaOH or citric acid/KOH in the same ratio with pH 4 to 6, or $KH_2PO_4$/Borax in the ratio 8:2 to 2:8 with pH 5.8 to 9.2, or $NH_3$/$NH_4Cl$ in the ratio 2:8 to 8:2 with pH 8 to 11, or a mixture of buffers.

25. An emulsion according to claim 1, wherein a thickening agent is additionally present in an amount of 0.1 to 1% by weight compared to the emulsion components.

26. An emulsion according to claim 1, wherein an antifreezing agent is additionally present in an amount of 1 to 10% by weight compared to the emulsion components.

27. An emulsion according to claim 1, wherein the concentration of the solvent is from 1 to 30% by weight.

28. A spray emulsion according to claim 4, wherein the pesticidally effective amount is from 0.01 to 1%.

* * * * *